United States Patent
Kyriakou

(10) Patent No.: US 9,805,465 B2
(45) Date of Patent: Oct. 31, 2017

(54) ANGIOGRAPHIC EXAMINATION FOR A VASCULAR SYSTEM IN A BODY REGION OF INTEREST OF A PATIENT

(71) Applicant: Yiannis Kyriakou, Spardorf (DE)

(72) Inventor: Yiannis Kyriakou, Spardorf (DE)

(73) Assignee: Siemens Aktiengesellschaft, München (DE)

( * ) Notice: Subject to any disclaimer, the term of this patent is extended or adjusted under 35 U.S.C. 154(b) by 320 days.

(21) Appl. No.: 14/606,381

(22) Filed: Jan. 27, 2015

(65) Prior Publication Data
US 2015/0213600 A1 Jul. 30, 2015

(30) Foreign Application Priority Data

Jan. 29, 2014 (DE) .................. 10 2014 201 559

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/032* (2013.01); *A61B 6/504* (2013.01); *A61B 6/5217* (2013.01);
(Continued)

(58) Field of Classification Search
None
See application file for complete search history.

(56) References Cited

U.S. PATENT DOCUMENTS 7,500,584 B2   3/2009   Schutz
7,500,784 B2   3/2009   Grebner et al.
(Continued)

FOREIGN PATENT DOCUMENTS

DE        10359431 A1    7/2004
DE    102005062445 A1    7/2007

OTHER PUBLICATIONS

German Office Action for related German Application No. 10 2014 201 559.6, mailed Aug. 20, 2014, with English Translation.
(Continued)

*Primary Examiner* — Barry Drennan
*Assistant Examiner* — Schiller Hill
(74) *Attorney, Agent, or Firm* — Lempia Summerfield Katz LLC

(57) ABSTRACT

The embodiments relate to an angiographic examination method for generating a 2D projection image. The method includes: (1) acquiring a volume dataset, (2) reconstructing a 3D volume from the volume dataset, (3) forward-projecting for generating a virtual vessel projection, (4) deriving a binary vessel mask, (5) acquiring at least one current 2D projection image, (6) combining the binary vessel mask with the at least one current 2D projection image to form a current mask, (7) thresholding the current mask to form a current binary mask, (8) back-projecting the current binary mask into the 3D volume to form a mask volume, (9) threshold value segmenting the mask volume in order to generate a final virtual vessel volume, and (10) subtracting a projection of the vessel volume from the current 2D projection images to generate a selective, overlay-free visualization of the body region of interest by selectable parameters.

20 Claims, 5 Drawing Sheets

(51) Int. Cl.
    *A61B 6/03*     (2006.01)
    *A61B 6/00*     (2006.01)
    *G06T 15/08*     (2011.01)
    *G06T 19/00*     (2011.01)
    *G06T 7/136*     (2017.01)

(52) U.S. Cl.
    CPC ............ *G06T 7/0016* (2013.01); *G06T 7/136* (2017.01); *G06T 15/08* (2013.01); *G06T 19/00* (2013.01); *A61B 6/481* (2013.01); *G06T 2207/10081* (2013.01); *G06T 2207/20224* (2013.01); *G06T 2207/30016* (2013.01); *G06T 2207/30101* (2013.01)

(56) References Cited

U.S. PATENT DOCUMENTS

| | | | | |
|---|---|---|---|---|
| 2001/0036303 | A1* | 11/2001 | Maurincomme | G06T 5/50 382/132 |
| 2006/0241369 | A1 | 10/2006 | Lienard et al. | |
| 2007/0140537 | A1* | 6/2007 | Heigl | G06T 15/08 382/128 |
| 2007/0183637 | A1 | 8/2007 | Kreuzer et al. | |
| 2008/0212857 | A1* | 9/2008 | Pfister | A61B 5/02007 382/130 |
| 2008/0247503 | A1 | 10/2008 | Lauritsch et al. | |
| 2011/0069063 | A1* | 3/2011 | Liao | G06T 7/33 345/419 |
| 2011/0235889 | A1* | 9/2011 | Spahn | A61B 6/4441 382/132 |
| 2012/0022951 | A1* | 1/2012 | Tolompoiko | G06Q 30/0241 705/14.68 |
| 2012/0218290 | A1* | 8/2012 | Waschbuesch | G09G 5/377 345/619 |
| 2013/0116551 | A1* | 5/2013 | Florent | A61B 6/12 600/424 |

OTHER PUBLICATIONS

John Brosky, Report from Europe: Siemens positions enhanced interventionalists, angiography Medical Device Daily, Tuesday, May 19, 2009 vol. 13, No. 95 p. 1 and 8 of 11, 2009.

Rossitti, S., Pfister, M.3D Road-Mapping in the Endovascular Treatment of Cerebral Aneurysms and Arteriovenous Malformations Interventional Neuroradiology, vol. 15, issue 3, pp. 283-290, 2009.

Siemens AG, Medical Solutions, Angiography, Fluoroscopic and Radiographic Systemssyngo iFlow / Dynamic Flow Evaluation / Answers for life. Order No. A91AX-20902-11C1-7600 | Printed in Germany | CC AX WS 12081.5 | © Dec. 2008, Siemens AG, 2008.

Siemens AG, Medical Solutions, Angiography, Fluoroscopic and Radiographic Systems, CaseStudies / Redefining 3D imaging during interventionsyngo DynaCT / syngo InSpace 3D / syngo iDentify / syngo iPilotOrder No. A91AX-20009-11C1-7600Printed in Germany, CC AX 20009 WS 10063, Oct. 2006, Siemens AG, 2006.

Siemens Medical Solutions, syngo iPilot—Effective guidance during interventional procedures; Flyer, Nov. 2005, Order No. A91AX-20004-11C-1-76, Nov. 1, 2005.

* cited by examiner

FIG 1  STATE OF THE ART
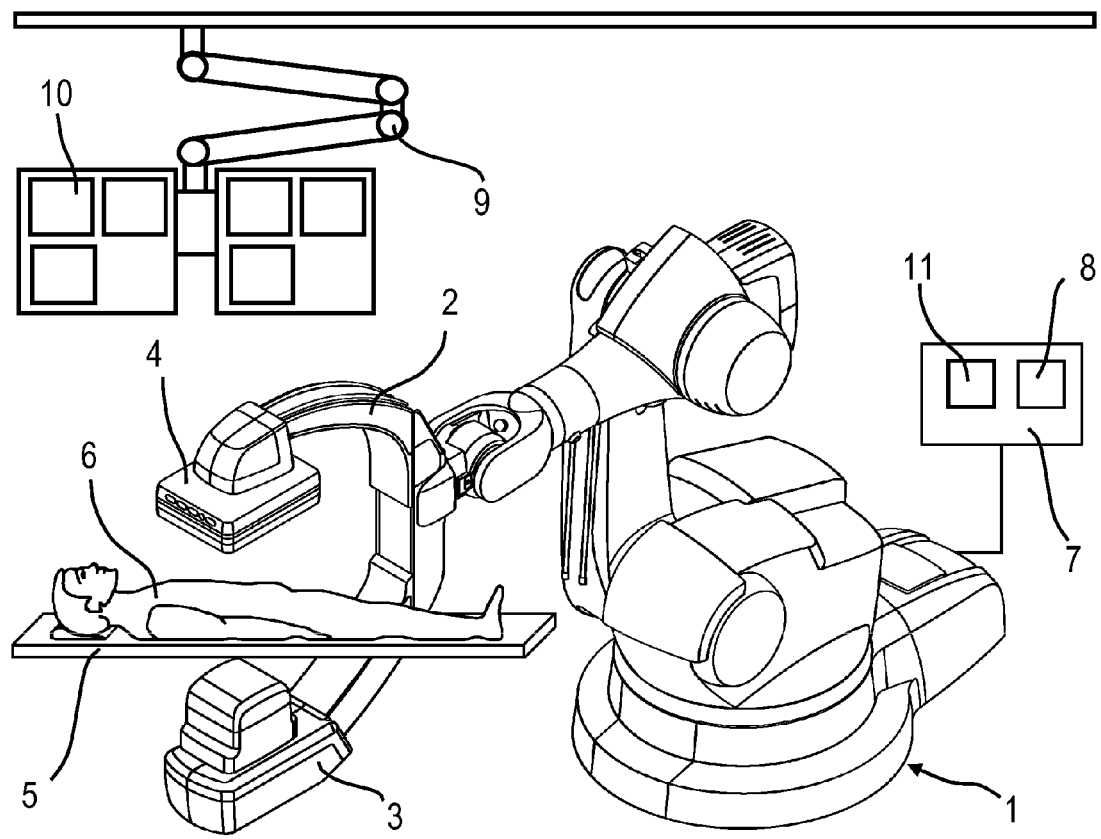
FIG 2  STATE OF THE ART
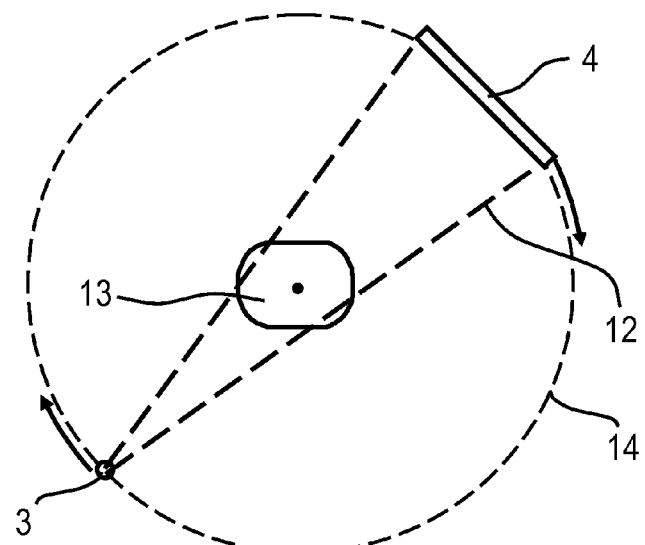

ANGIOGRAPHIC EXAMINATION FOR A VASCULAR SYSTEM IN A BODY REGION OF INTEREST OF A PATIENT

CROSS-REFERENCE TO RELATED APPLICATIONS

This application claims the benefit of DE 10 2014 201 559.6, filed on Jan. 29, 2014, which is hereby incorporated by reference in its entirety.

TECHNICAL FIELD

The embodiments relate to an angiographic examination method for generating at least one 2D (two-dimensional) projection image of a vascular system in a body region of interest of a patient by an angiography system. An overlay-free, multi-parametric visualization of the brain parenchyma, for example, may be obtained by the angiographic examination method.

BACKGROUND

Two-dimensional DSA series may be used to provide a color-coded visualization of the bolus arrival time (time-to-peak (TTP)), as is described for example in "syngo iFlow/Dynamic Flow Evaluation/Answers for life," published by Siemens AG, Medical Solutions, Angiography, Fluoroscopic and Radiographic Systems, Order No. A91AX-20902-11C1-7600. Although the vascular tree may be very well visualized, it is sometimes important, in the event of stroke or vasospasm, for example, to see only the perfusion or blood circulation in the brain parenchyma. This is not possible in most cases, since the large vessels overlie the regions and may not be separated therefrom. It is not always desirable to perform a perfusion CT scan or a perfusion acquisition by rotational angiography.

If a segmentation of the parenchyma and the vessels exists, it is furthermore possible to superimpose a graphical multicomponent overlay onto the current DSA series in 2D or 3D for use as a navigation aid.

FIG. 1 depicts a single-plane X-ray system, presented by way of example, including a C-arm 2 in the form of a six-axis industrial or articulated-arm robot supported by a stand 1, to the ends of which are attached an X-radiation source, for example, an X-ray emitter 3, including X-ray tube and collimator, and an X-ray image detector 4 as image acquisition unit.

The articulated-arm robot, known for example from U.S. Pat. No. 7,500,784 B2, which may have six axes of rotation and consequently six degrees of freedom, provides the C-arm 2 to be adjusted in an arbitrary manner in space, (e.g., by the C-arm being rotated about a center of rotation between the X-ray emitter 3 and the X-ray image detector 4). The angiographic X-ray system 1 to 4 may be able to be rotated about centers of rotation and axes of rotation in the C-arm plane of the X-ray image detector 4, such as about the center point of the X-ray image detector 4 and about axes of rotation that intersect the center point of the X-ray image detector 4.

The known articulated-arm robot has a base frame that is permanently installed on a floor, for example. Attached thereto is a turntable that is rotatable about a first axis of rotation. Mounted on the turntable, so as to be pivotable about a second axis of rotation, is a robotic floating link to which is attached a robotic arm that is rotatable about a third axis of rotation. Mounted to the end of the robotic arm is a robotic hand that is rotatable about a fourth axis of rotation. To secure the C-arm 2, the robotic hand has an attachment element that is pivotable about a fifth axis of rotation and is able to be rotated about a sixth axis of rotation extending at right angles thereto.

The implementation of the X-ray diagnostic apparatus is not contingent on the industrial robot. Conventional C-arm devices may also be used.

The X-ray image detector 4 may be a flat semiconductor detector, rectangular or square in shape, which may be produced from amorphous silicon (a-Si). Integrating and possibly counting CMOS detectors may also be used.

A patient 6 to be examined is positioned as examination subject in the beam path of the X-ray emitter 3 on a tabletop platform 5 of a patient support table. Connected to the X-ray diagnostic apparatus is a system control unit 7 having an imaging system 8 that receives and processes the image signals of the X-ray image detector 4. The X-ray images may then be viewed on displays of a monitor array 10 retained by a ceiling-mounted, longitudinally displaceable, pivotable, rotatable and height-adjustable carrier system 9. Also provided in the system control unit 7 is a device 11 in which the method described herein below may be performed.

Instead of the X-ray system having the stand 1 in the form of the six-axis industrial or articulated-arm robot depicted by way of example in FIG. 1, the angiographic X-ray system may also have, as illustrated in a simplified schematic in FIG. 2, a conventional ceiling- or floor-mounted support for the C-arm 2.

Instead of the C-arm 2 depicted by way of example, the angiographic X-ray system may also have separate ceiling and/or floor-mounted supports for the X-ray emitter 3 and the X-ray image detector 4, which are coupled for example in an electronically rigid manner.

The X-ray emitter 3 emits a beam of radiation 12 that exits from a beam focus of its X-radiation source and impinges on the X-ray image detector 4. If 3D datasets are to be generated in accordance with the so-called DynaCT method, a rotational angiography method, the rotatably mounted C-arm 2 is rotated together with X-ray emitter 3 and X-ray image detector 4 such that, as FIG. 2 depicts schematically in a plan view onto the axis of rotation, the X-ray emitter 3, represented in this case illustratively by its beam focus, and the X-ray image detector 4 travel on a circular path 14 around an examination subject 13 located in the beam path of the X-ray emitter 3. The circular path 14 may be traversed completely or partially for the purpose of generating a 3D dataset or volume dataset.

The C-arm 2 together with X-ray emitter 3 and X-ray image detector 4 moves in this configuration in accordance with the DynaCT method, such as through at least an angular range of 180°, (e.g., 180° plus fan angle), and acquires projection images in quick succession from different projections. The reconstruction may be effected only from a subset of the acquired data.

The subject 13 that is to be examined may be, for example, an animal or human body, but also a phantom body.

The X-ray emitter 3 and the X-ray image detector 4 each rotate around the subject 5 in such a way that the X-ray emitter 3 and the X-ray image detector 4 are disposed on opposite sides of the subject 13.

In conventional radiography or fluoroscopy using an X-ray diagnostics apparatus, the medical 2D data of the X-ray image detector 4 is buffered in the imaging system 8 if necessary and subsequently displayed on the monitor 9.

SUMMARY AND DESCRIPTION

The scope of the present invention is defined solely by the appended claims and is not affected to any degree by the statements within this summary. The present embodiments may obviate one or more of the drawbacks or limitations in the related art.

The object underlying the embodiments is to embody an angiographic examination method of the type cited in the introduction in such a way that an overlay-free visualization of the brain parenchyma may be generated in 2D DSA series.

The object is achieved for an angiographic examination method by the following acts: (S1) acquisition of a volume dataset of the body region of interest containing the vascular system; (S2) reconstruction of a 3D volume from the volume dataset containing the vascular system; (S3) forward-projection for generating a virtual projection containing the vessels; (S4) derivation of a binary vessel mask from the virtual projection; (S5) acquisition of at least one current 2D projection image; (S6) combination of the binary vessel mask with the at least one 2D projection image in order to form a current mask; (S7) thresholding of the current mask in order to form a current binary mask; (S8) back-projection of the current binary mask into the 3D volume in order to form a mask volume; (S9) threshold value segmentation of the mask volume in order to generate a final virtual vessel volume, and (S10) subtraction of a projection of the vessel volume from the current 2D projection images in order to generate a selective, overlay-free visualization of the body region of interest with selectable parameters.

By this method, the user is able to choose whether he or she wishes to see brain parenchyma only or vessels only, or a combination thereof. It is furthermore possible to combine different parameters in a single visualization.

The acquisition of a volume dataset according to method act Si may advantageously be accomplished by a rotational angiography scan.

Further processing is simplified if method act S2 includes a segmentation of the vascular system.

It has proven advantageous if the virtual projection according to method act S3 is a virtual 2D DSA.

In certain embodiments, the current 2D projection images may be sourced from a current measured 2D DSA series.

The 2D projection images currently acquired according to method act S5 may advantageously be maximum opacification images of a 2D DSA series.

In certain embodiments, intensities and optimization may be adjusted prior to method act S10.

The visibility of the individual image portions may be increased if, for the selective, overlay-free visualization of the body region of interest, the transmittance factors of the portions that are to be overlaid are adjustable, in particular separately adjustable.

It has proven advantageous if an adjustment device is provided for the separate adjustment of the transmittance factors and is configured such that transmittance bars indicating the adjustment may be inserted.

In certain embodiments, the adjustment device may be configured in such a way that the transmittance factors may be set by moving the sliders with the mouse.

The performed adjustment may be made more recognizable if a digital percentage indicator is assigned to the transmittance bars in order to indicate the portions that are to be overlaid.

BRIEF DESCRIPTION OF THE DRAWINGS

FIG. 1 depicts an embodiment of a known C-arm angiography system having an industrial robot as carrier device.
FIG. 2 depicts a schematic view of the geometric relationships in rotational angiography by the C-arm angiography system according to FIG. 1.

DETAILED DESCRIPTION

Figure 3:
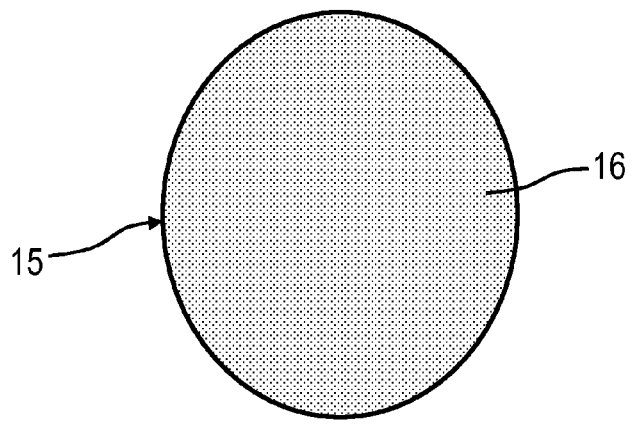
FIG. 3 depicts an embodiment of a mask image.

The DSA principle will now be explained with reference to FIGS. 3 to 5. Firstly, a mask image 15 of a head is acquired in which the entire anatomy 16, such as also cranial bone for example, is contained. Following an injection of contrast agent, a fill image 17 (FIG. 4) is generated in which, in addition to an anatomical background 18, (e.g., the anatomy 16 according to FIG. 3), the parenchyma 19 and the vessels 20 are now also apparent. If these two images are now subtracted from each other, a DSA image 21, depicted in FIG. 5, is obtained, which depicts only the regions filled with contrast agent, (e.g., the parenchyma 19 and the vessels 20).

A reconstructed 3D volume 22 containing a vascular tree or vascular system 23, acquired for example by a computed tomography angiography (CTA) or a rotational angiography scan, is converted by forward-projection 24 into a virtual vessel projection 25 (e.g., 2D DSA (digital subtraction angiography)) in which the vascular tree containing the vessels 20 may already be segmented. A virtual binary vessel mask 26 is determined therefrom.

The binary vessel mask 26, which represents the entire vascular tree, is combined with projection images acquired from the current measured 2D DSA series, (e.g., the maximum opacification image 27 if an iFlow combination is desired subsequently). The maximum opacification image 27 is described in the publication cited hereinabove. For each pixel, the image reproduces the maximum opacity due to a contrast agent during the entire fill phase.

From this combination, a mask 28 is formed, which is converted by thresholding 29 into a binary mask 30. By back-projection 31 of the binary mask 30 into the reconstructed 3D volume 22, a mask volume 32 is obtained, which is subsequently post-processed by a threshold value segmentation 33 in order to generate a final virtual vessel volume 34. This corresponds to a volume adjusted to and reflecting the status of the current 2D DSA series.

Figure 6:
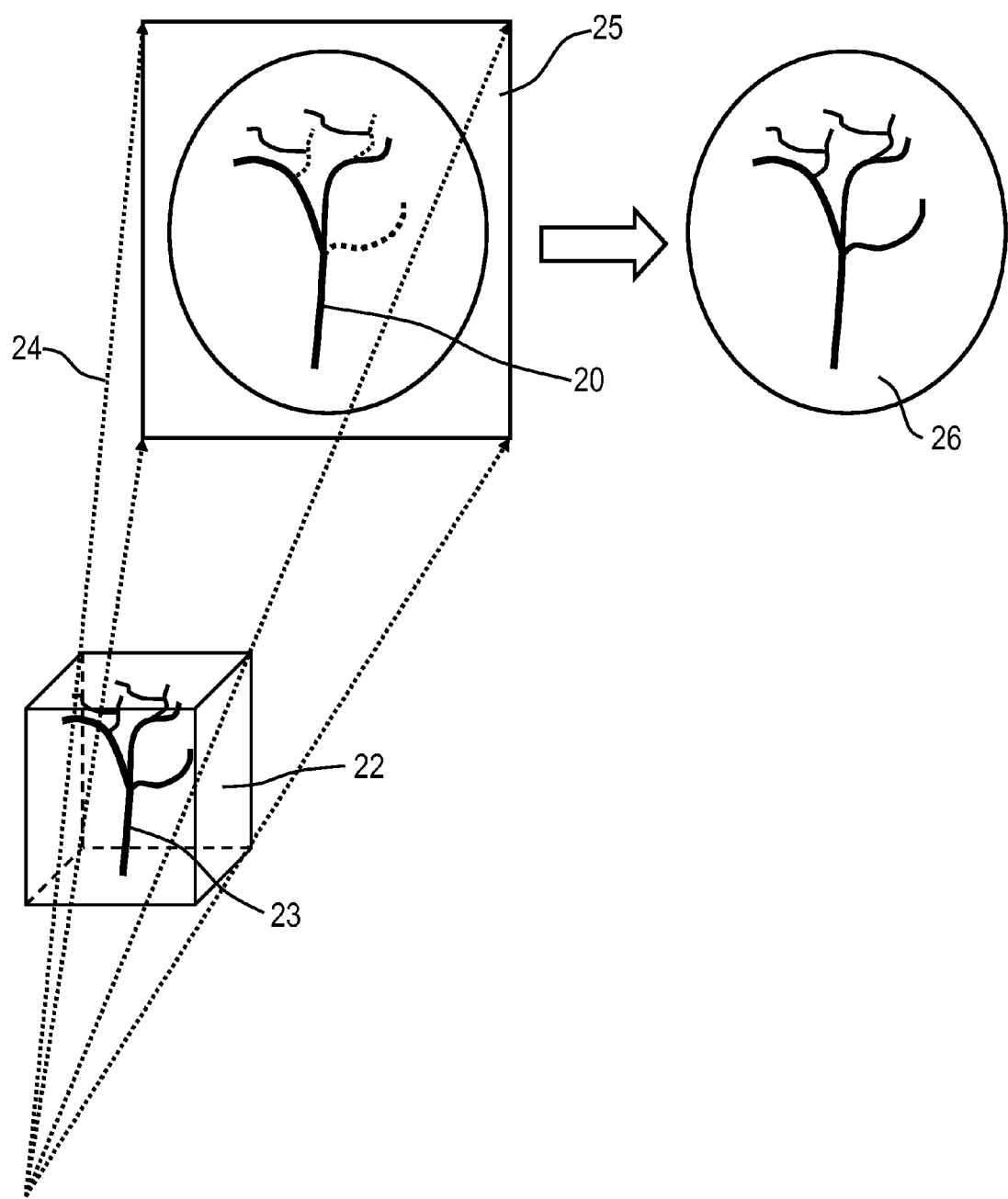
FIG. 6 depicts an embodiment of a projection for forming a virtual binary mask.
Figure 7:
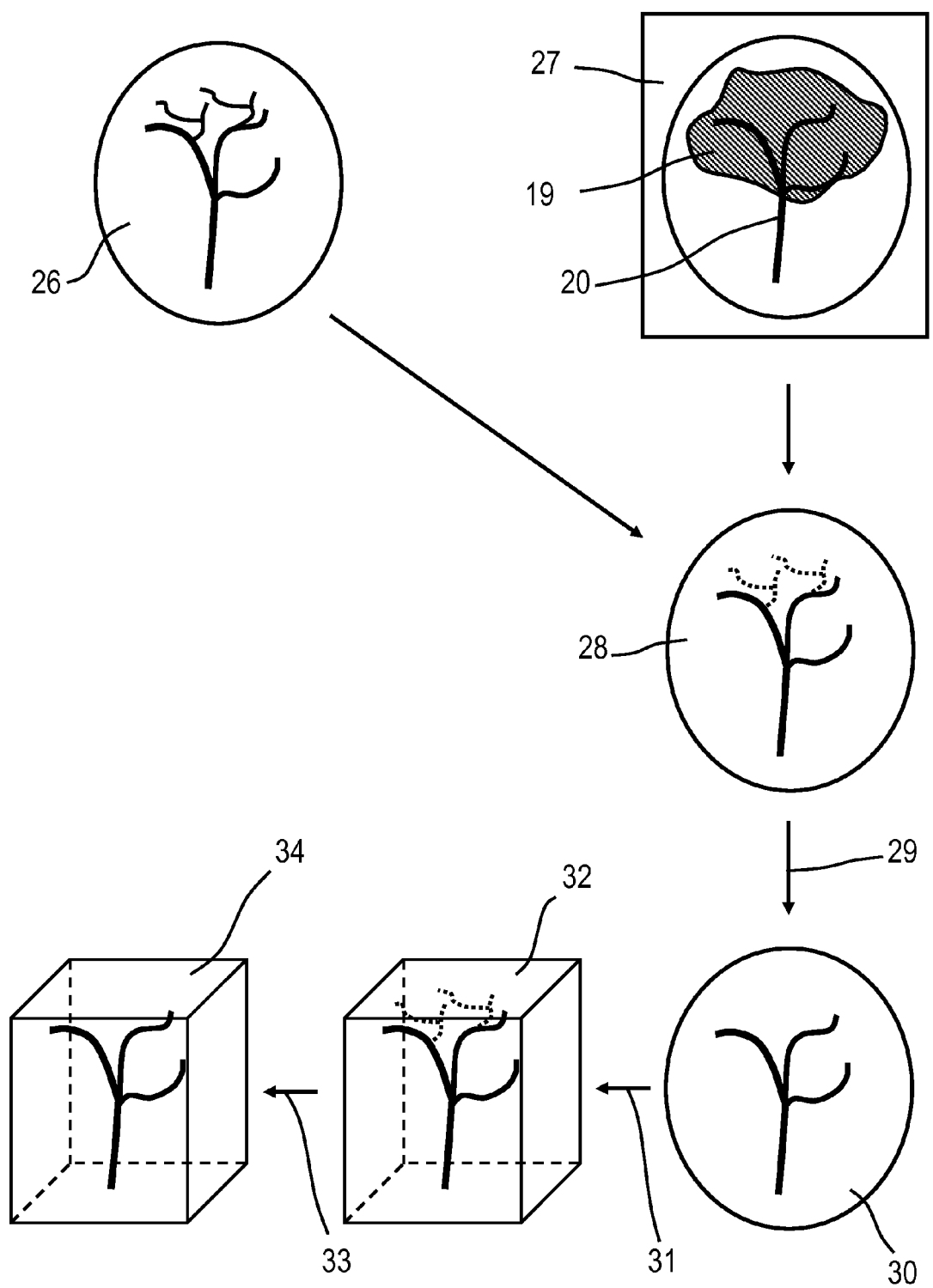
FIG. 7 depicts an embodiment of a representation of the method acts for forming a volume adjusted to the status of the current 2D DSA series and reflecting the same.

This may be followed by an adjustment of intensities and an optimization whereby, starting from the acquisition of the reconstructed 3D volume 22 (f1) for a viewing angle α and acquisition of the DSA series 27 p(α) for the iFlow evaluation, the final virtual vessel volume 34 (f2) is generated in accordance with the description with reference to FIGS. 6 and 7. A forward-projection is performed from:

$$f2(\alpha) \rightarrow p2(\alpha)$$

with an iterative minimization, for example by gradient descent:

$$X(p2(\alpha))-[p(\alpha)*M2] \rightarrow \min$$

in which the factor X is adjusted.

The factor X is a parametric basis function, (e.g., polynomial), for adjusting the forward-projected intensities, albeit in its simplest form, however, a scaling factor (scalar).

In this case $X(p2(\alpha))$ is used in order to subtract only the vessels 20: Since $X(p2(\alpha))$ is a volume, this may be done for arbitrary angulations or subseries. A partial subtraction of the vessels 20 is also possible by adjusting the volume accordingly.

Figure 4:
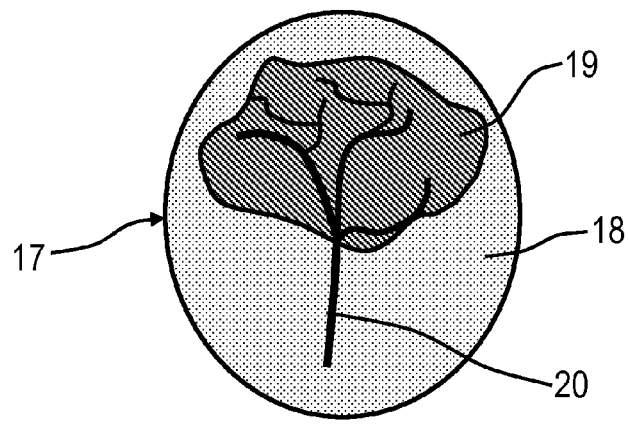
FIG. 4 depicts an embodiment of a fill image.
Figure 5:
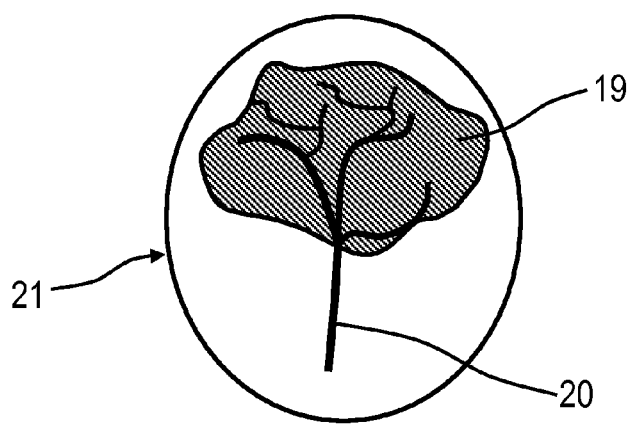
FIG. 5 depicts an embodiment of a DSA image.
Figure 8:
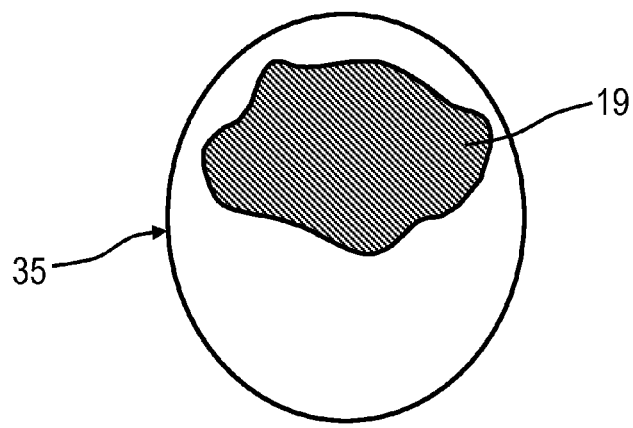
FIG. 8 depicts an embodiment of a brain parenchyma visualization.

Thus, starting from the DSA fill image 17 according to FIG. 4, a progression is made to an overlay-free brain parenchyma visualization 34 of the parenchyma 19, depicted in FIG. 8, which may very well be used for post-processing for example with syngo iFlow.

Figure 9:
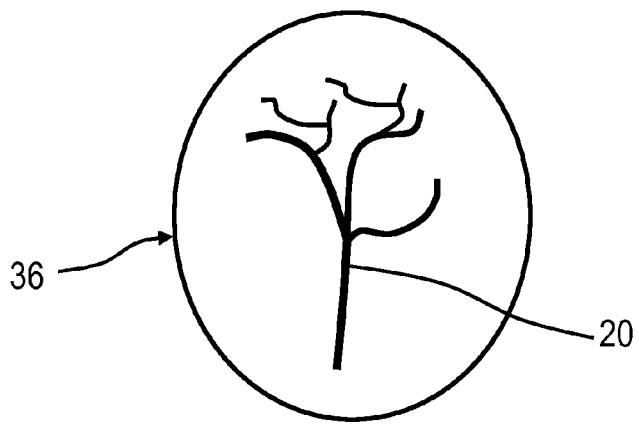
FIG. 9 depicts an embodiment of a vessel image.

Starting from the DSA fill image 17 according to FIG. 4, however, it is also possible, in addition to separating the parenchyma 19, to extract the vessels 20 only and visualize the same in a vessel image 33, as is depicted in FIG. 9.

If it is now aimed to provide a further improved visualization in which it is possible to choose whether to see only parenchyma 19 or only vessels 20, or a combination thereof, transmittance bars 38 to 40 may be provided. In such an embodiment, the bar 38 for brain parenchyma, the bar 39 for anatomical background, and the bar 40 for vessels indicate the respective transmittance factor. On the other hand, the transmittance bars 38 to 40, in the form of sliders 41 for example, may be used to enable the transmittance factors to be adjusted separately. This enables many combinations of different parameters to be realized in a simple manner for example by moving the sliders 41 with the mouse. In addition, a digital percentage indicator 42 may also be assigned to the transmittance bars 38 to 40.

An important building block described with reference to FIGS. 3 to 7 is the generation of a vessel volume f2 with the aid of the original 3D volume f1, (e.g., a 3D rotational angiography or a computed tomography angiography (CTA) scan), and the current DSA series. The volume f2 includes only the vessels that are also to be found in the DSA. The differences between 2D and 3D may be manifold, e.g., different injection, injection site, contrast agent concentration, etc.

A 3D acquisition is to be recommended that is as close as possible to the 2D series, alternatively an IV 3D rotational angiography acquisition, in which many vessels (e.g., arteries and veins) are imaged thereby which will be selectively removed according to the method as described with reference to FIGS. 6 and 7.

The vessel segmentation in the 3D volume is given by the nature of the 3D datasets, specifically in the 3D DSA technique. By a forward-projection 24, a virtual vessel projection 25 is generated that exhibits a different vessel configuration from the current series. From the virtual vessel projection 25, a vessel mask 26 is generated and combined (e.g., if an iFlow combination is desired subsequently) with the current DSA series, (e.g., a maximum opacification image 27). This results in the mask 28, which is subsequently binarized to form the mask 30. The binary mask 30 is back-projected into the volume 22 and subsequently post-processed by a threshold value segmentation 33 in order to generate the final virtual volume 34. This is equivalent to a volume that corresponds to and reflects the status of the current 2D DSA series.

Because the intensities have not been adjusted and the intensities or, as the case may be, the attenuation due to the vessels are to be selectively subtracted subsequently, the described adjustment of intensities and optimization is applied. In this case, the intensity differences that may arise for example as a result of a different concentration of the contrast agent or other blood flow conditions are minimized. The basis function X is used as a correction function in order subsequently to implement the subtraction of the vessels as accurately as possible at the intensity level.

Thereafter, the subtraction may be performed in order to visualize only the parenchyma 19 according to FIG. 8, in which case partial subtractions, (e.g., only arteries or only veins), are also possible in that an additional segmentation or selection takes place in $X(p2(\alpha))$.

The starting point for an overlaying of a multi-parametric visualization of the vessel geometry, of the anatomical background, and of the brain parenchyma within a DSA series is a successful segmentation of the parenchyma and the vessel configuration, as has been described for example with reference to FIGS. 6 and 7. In addition, a 3D segmentation of the vessels may be used here for the vessel configuration, which 3D segmentation is forward-projected in 2D for the corresponding geometry analogously to the method according to syngo iPilot, which is described in brief in the flyer titled "syngo iPilot—Effective guidance during interventional procedures," published by Siemens AG, Medical Solutions, 2005/11, Order No. A91AX-20004-11C-1-76, or "CaseStudies/Redefining 3D imaging during intervention/syngo DynaCT/syngo InSpace 3D/syngo iDentify/syngo iPilot," published by Siemens AG, Medical Solutions, Order No. A91AX-20009-11C1-7600, CC AX 20009 WS 10063, 10.2006.

The superposition of the vessels is performed as an overlay onto the parametric map from the dynamic 2D angiography (2D DSA). This may be a color-coded visualization of the average throughflow time (MTT (mean transit time)) or maximum time (TTP (time to peak)), which may be calculated from the dynamic data. The vessel geometry may be superimposed and if necessary varied using a different form of visualization, e.g. rendering. This may either be the vessels from the segmentation or the 3D data results from a 3D angiography dataset analogously to the use of syngo iPilot.

In addition, the thus decoupled images may represent different parameters. Accordingly, for example, the vessel overlay may represent the TTP values, and the underlying parenchyma visualization the MTT.

Figure 10:
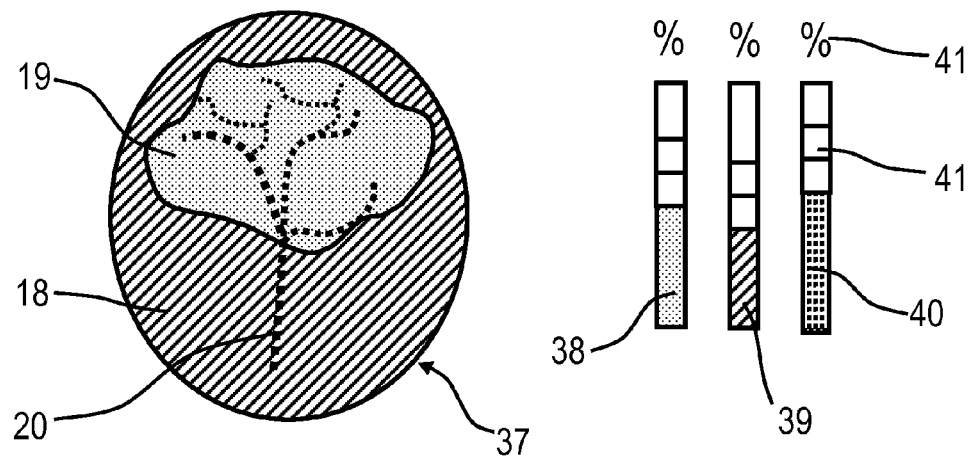
FIG. 10 depicts an embodiment of a composite image with graphical overlay with fading indicator.

At the same time the anatomical background, (e.g., the osseous structures), is maintained as a third independent image and also used as an overlay, such that a triple overlay image with different mixing ratios may result, as is depicted for example in FIG. 10.

The following are achieved by the method: (1) a "vessel" overlay-free DSA visualization, for example for a parametric and color-coded representation, (2) a use as an iFlow image for the blood flow parameter calculation in the (brain) parenchyma, for example in TTP (Time to Peak) visualizations, (3) a use also for other body regions if movements and/or other major changes are compensated, (4) a possible use of partial subtractions in order to visualize only certain portions of the brain without vessels, and (5) an arbitrary angulation selection by 3D and/or an iterative adjustment of the intensities in order to avoid subtraction artifacts.

Furthermore, the method provides: (1) a combination visualization composed of angiography and parenchyma imaging, (2) an overlay of the vessels on parametric maps as a "roadmap" function, (3) a decoupling of the macroscopic and microscopic perfusion so that different parameters may be calculated and visualized, (4) an inclusion and exclusion of the vascular tree, (5) a 3D integration by a combination with for example syngo iPilot, and/or (6) a triple overlay functionality.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. An angiographic examination method for generating at least one 2D projection image of a vascular system in a body region of interest of a patient by an angiography system, the method comprising:
acquiring a volume dataset of the body region of interest containing the vascular system;
reconstructing a 3D volume from the volume dataset containing the vascular system;
forward-projecting to generate a virtual vessel projection;
deriving a binary vessel mask from the virtual vessel projection;
acquiring at least one current 2D projection image;
combining the binary vessel mask with the at least one current 2D projection image to form a current mask;
thresholding the current mask to form a current binary mask;
back-projecting the current binary mask into the 3D volume to form a mask volume;
threshold value segmenting the mask volume to generate a final virtual vessel volume; and
subtracting a projection of the vessel volume from the current 2D projection images to generate a selective, overlay-free visualization of the body region of interest by selectable parameters.

2. The angiographic examination method as claimed in claim 1, wherein the acquisition of the volume dataset is accomplished by rotational angiography.

3. The angiographic examination method as claimed in claim 2, wherein the reconstructing includes a segmentation of the vascular system.

4. The angiographic examination method as claimed in claim 3, wherein the virtual vessel projection is a virtual 2D DSA.

5. The angiographic examination method as claimed in claim 4, wherein the current 2D projection images are sourced from a current measured 2D DSA series.

6. The angiographic examination method as claimed in claim 5, wherein the subtracting of the projection is preceded by an adjustment of intensities and optimization.

7. The angiographic examination method as claimed in claim 6, wherein transmittance factors of image portions that are to be overlaid are adjustable for the selective, overlay-free visualization of the body region of interest.

8. The angiographic examination method as claimed in claim 1, wherein the reconstructing includes a segmentation of the vascular system.

9. The angiographic examination method as claimed in claim 1, wherein the virtual vessel projection is a virtual 2D DSA.

10. The angiographic examination method as claimed in claim 1, wherein the current 2D projection images are sourced from a current measured 2D DSA series the segmented thrombosed section of the blood vessel with the fluoroscopic images.

11. The angiographic examination method as claimed in claim 10, wherein the current 2D projection images are maximum opacification images of the 2D DSA series.

12. The angiographic examination method as claimed in claim 1, wherein the subtracting of the projection is preceded by an adjustment of intensities and optimization.

13. The angiographic examination method as claimed in claim 1, wherein transmittance factors of image portions that are to be overlaid are adjustable for the selective, overlay-free visualization of the body region of interest.

14. The angiographic examination method as claimed in claim 13, wherein the transmittance factors are separately adjustable.

15. The angiographic examination method as claimed in claim 14, wherein an adjustment device is provided for the separate adjustment of the transmittance factors and the adjustment device is configured such that transmittance bars indicating the adjustment may be inserted.

16. The angiographic examination method as claimed in claim 15, wherein the transmittance bars are sliders.

17. The angiographic examination method as claimed in claim 13, wherein an adjustment device is provided for the separate adjustment of the transmittance factors and the adjustment device is configured such that transmittance bars indicating the adjustment may be inserted.

18. The angiographic examination method as claimed in claim 17, wherein the transmittance bars are sliders.

19. The angiographic examination method as claimed in claim 18, wherein the adjustment device is configured such that the transmittance factors are adjusted by moving the sliders with a mouse.

20. The angiographic examination method as claimed in claim 14, wherein a digital percentage indicator is assigned to transmittance bars in order to indicate the image portions that are to be overlaid.

* * * * *